United States Patent
Kwon et al.

(10) Patent No.: US 10,591,487 B2
(45) Date of Patent: Mar. 17, 2020

(54) SMALL MOLECULE DETECTION AND LOCALIZATION METHOD BASED ON MALDI IMAGING MASS SPECTROMETRY

(71) Applicant: INDUSTRY-ACADEMIC COOPERATION FOUNDATION, YONSEI UNIVERSITY, Seoul (KR)

(72) Inventors: Ho Jeong Kwon, Seoul (KR); Yonghyo Kim, Seoul (KR); György Marko-Varga, Malmo (SE)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 310 days.

(21) Appl. No.: 15/333,315

(22) Filed: Oct. 25, 2016

(65) Prior Publication Data

US 2017/0115306 A1    Apr. 27, 2017

(30) Foreign Application Priority Data

Oct. 26, 2015 (KR) .................. 10-2015-0148837

(51) Int. Cl.
*G01N 33/68* (2006.01)
*G01N 33/94* (2006.01)
*G01N 33/566* (2006.01)

(52) U.S. Cl.
CPC ......... *G01N 33/6851* (2013.01); *G01N 33/94* (2013.01); *G01N 2333/71* (2013.01)

(58) Field of Classification Search
CPC . G01N 2333/71; G01N 33/6851; G01N 33/94
See application file for complete search history.

(56) References Cited

U.S. PATENT DOCUMENTS

2014/0303148 A1* 10/2014 Kwon .................. A61K 31/407
514/214.02

FOREIGN PATENT DOCUMENTS

WO    WO 2013/081374    *  6/2013

OTHER PUBLICATIONS

Torok et al., "Localization of sunitinib, its metabolites and its target receptors in tumour-bearing mice: a MALDI-MS imaging study," Br. J. Pharmacol., Feb. 2015, vol. 172, No. 4, pp. 1148-1163; Epub Jan. 12, 2015.*
Kwon et al., "Drug compound characterization by mass spectrometry imaging in cancer tissue," Arch Pharm Res. Sep. 2015; vol. 38, No. 9, pp. 1718-1727; Epub Jul. 23, 2015.*
A print-out "Thermo Fisher Scientific LTQ Orbitrap XL" retrieved from https://assets.thermofisher.com/TFS-Assets/CMD/Specification-Sheets/PS-30133-MS-LTQ-Orbitrap-XL-PS30133-EN.pdf on Oct. 2, 2018.*
Reyzer et al., "Early Changes in Protein Expression Detected by Mass Spectrometry Predict Tumor Response to Molecular Therapeutics," Cancer Research, 2004, vol. 64, pp. 9093-9100.*
Marko-Varga et al., "Drug localization in different lung cancer phenotypes by MALDI mass spectrometry imaging," J. Proteomics, 2011, vol. 74, No. 7, pp. 982-992.*
Lee et al., "Differential effects of VEGFR-1 and VEGFR-2 inhibition on tumor metastases based on host organ environment," Cancer Res., 2010, vol. 70, No. 21, pp. 8357-8367.*

* cited by examiner

*Primary Examiner* — Galina M. Yakovleva
(74) *Attorney, Agent, or Firm* — Amster, Rothstein & Ebenstein LLP

(57) ABSTRACT

Disclosed is a angiogenesis inhibition determining method using MALDI mass spectrometry, and more particularly, relate to a method for detecting whether small molecules are bound with a target protein and for measuring a binding distribution between the small molecules and the target protein by comparing a result of MALDI mass spectrometry with a result of immunofluorescence of the small molecules, which are used as drugs, for the target protein, and for determining as angiogenesis is inhibited in a portion overlapping with a portion where the drug small molecules are present after the MALDI mass spectrometry in the cell or in the biosample including organelles and a portion where the target protein is present after immunofluorescence, as well as for detecting presence or absence and a distribution state of small molecules used as drugs in a sample by using MALDI mass spectrometry.

4 Claims, 15 Drawing Sheets

SMALL MOLECULE DETECTION AND LOCALIZATION METHOD BASED ON MALDI IMAGING MASS SPECTROMETRY

CROSS-REFERENCE TO RELATED APPLICATIONS

A claim for priority under 35 U.S.C. § 119 is made to Korean Patent Application No. 10-2015-0148837 filed Oct. 26, 2015, in the Korean Intellectual Property Office, the entire contents of which are hereby incorporated by reference.

BACKGROUND

Embodiments of the inventive concept described herein relate to a small molecule detection and localization method based on Matrix-Assisted Laser Desorption Ionization (MALDI) imaging mass spectrometry, and more particularly, relate to a method for detecting whether small molecules are bound with a target protein and for measuring a binding distribution between the small molecules and the target protein in a cell or in a biosample including organelles by comparing a result of MALDI mass spectrometry with a result of immunofluorescence of the small molecules, which are used as drugs, for the target protein, and for determining as angiogenesis is inhibited in a portion overlapping with a portion where the drug small molecules are present after the MALDI mass spectrometry in the cell or in the biosample including organelles and a portion where the target protein is present after immunofluorescence, as well as for detecting presence or absence and a distribution state of small molecules used as drugs in a sample by using MALDI mass spectrometry.

In general, a mass spectrometer is a spectrometer for measuring mass of a compound, determining a molecular weight of a compound by measuring mass-to-charge quantity after electrically charging and ionizing a compound. Since the first use of mass spectrometry in the early 1900s, various ionization methods have been developed and proposed for mass spectrometry of nonvolatile or thermounstable materials, for example, including SIMS, FD, FAB, MALDI, and so on.

The histology-directed Matrix-Assisted Laser Desorption Ionization (MALDI) imaging mass spectrometry developed by Richard M. Caprioli is an imaging mass spectrometry using MALDI, obtaining mass spectrometry information directly from a tissue through MALDI by coating a matrix on the surface of the tissue which is to be inspected.

While the beginning of applying MALDI directly to a human anatomy is recent years, there has been a report that inspecting a frozen tissue by using sinapinic acid as a matrix may provide useful information (Lancet 2003; 362(9382): 433-449, Cancer Res 2005; 65(17): 7674-7681, Mol Cell Proteomics 2006; 5: 1975-1983).

A crude extract of *Tabernaemontana catharinensis* including voacangine has been reported as a powerful anticancer agent (C. G. Pereira, J. E. Carvalho, M. A. A. Meireles, Anticancer activity of *Tabernaemontana catharinensis* extract obtained by supercritical fluid extraction, Rev. Bras. Pl. Med., Botucatu, V. 8, N. 4 (2006), 144-149). Additionally, voacangine is known as dose-dependently inhibiting capsaicin-induced contraction (M. W. Lo, Matsumoto, M. Iwai, K. Tashima, M. Kitajima, S. Hone, H. Takayama, Inhibitory effect of iboga-type indole alkaloids on capsaicin-induced contraction in isolated mouse rectum, J. Nat. Med. 65 (2011) 157-165).

The inventors found for the first time that voacangine was a new natural small-molecular compound inhibiting in vitro and in vivo angiogenesis by a nontoxic dose. The inventors screened 300 crude extracts which are taken from a natural plant that is effective in proliferating Human Umbilical Vascular Endothelial Cell (HUVEC) by using a cell-based screening technique. As a result of the screening, the inventors found that voacangine as a new natural small-molecular compound is characterized in anti-angiogenesis.

Additionally, since voacangine dose-dependently inhibited expression levels of HIF-1α and VEGF that is a target gene of HIF-1α and thereby inhibited VEGF-induced angiogenic responses without cell toxicity in low concentration through inhibition of expression of angiogenesis inhibition factors, the inventors verified that voacangine could peculiarly disturb an angiogenesis signaling process.

However, in the case that voacangine showing such general functions is injected into a biotissue, there has not been proposed any technology for detection of its presence or absence and for measurement of its distribution state in a cell.

SUMMARY

Embodiments of the inventive concept provide a method for detecting whether specific small molecules are bound with a target protein in a cell or in a biosample including organelles and for measuring a distribution of binding between the small molecules and the target protein in the cell or in the biosample including organelles, by comparing a result of inspecting the target protein with a result of MALDI mass spectrometry as well as by detecting the small molecules including voacangine, and then for determining to induce and/or inhibit angiogenesis from the measured results.

Embodiments of the inventive concept provide a method for detecting a specific drug and small particles, which are known as being bound with the drug, in a cell or a biosample including organelle by using MALDI mass spectrometry, which is used for simple mass spectrometry, and for determining to inhibit angiogenesis from the detected result.

According to an aspect of an embodiment, an angiogenesis inhibition determining method using MALDI mass spectrometry includes preparing a sample, treating a drug in the sample, performing MALDI mass spectrometry for the drug-treated sample, detecting a target protein for the drug in the prepared sample by immunofluorescence, comparing a result of the MALD mass spectrometry with a result of immunofluorescence for the target protein, and determining that angiogenesis is inhibited in a portion overlapping with a portion where the small molecules are present after the MALDI mass spectrometry and a portion where the target protein is present after immunofluorescence.

In the angiogenesis inhibition determining method using MALDI mass spectrometry, the treated drug may be voacangine given in Formula 1 as follows:

<Formula 1>

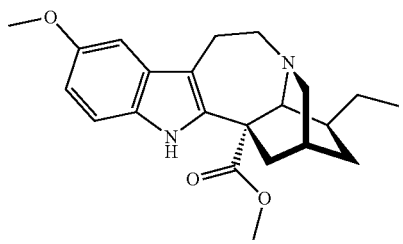

In an angiogenesis inhibition determining method using MALDI mass spectrometry according to embodiments of the inventive concept, the drug may be adopted in various kinds except the voacangine.

In the angiogenesis inhibition determining method using MALDI mass spectrometry according to embodiments of the inventive concept, the MALDI mass spectrometry for the voacangine-treated sample may show peaks in 360 to 380 m/z, 330 to 340 m/z, and 300 to 310 m/z.

In embodiments, a mass value measured through MALDI mass spectrometry may include an error range of ±0.1 m/z. This is because there may be some a little error in measured mass values in accordance with various experimental circumstances. For example, the mass value of 360.0 m/z may be construed as practically having a range of 359.9 to 360.1 m/z. The error range may be ±0.5 m/z.

In the angiogenesis inhibition determining method using MALDI mass spectrometry according to embodiments of the inventive concept, the MALDI mass spectrometry for the voacangine-treated sample may show a main peak at 369.21 m/z and may show peaks at 336.24 m/z and 309.31 m/z. The peaks shown at the 336.24 m/z and 309.31 m/z are shown as being expressed due to fragments which are generated through metabolism in a tissue after treatment of voacangine.

In an angiogenesis inhibition determining method using MALDI mass spectrometry according to embodiments of the inventive concept, the MALDI mass spectrometry is characterized in using a MALDI imaging mass spectrometer. In an angiogenesis inhibition determining method using MALDI mass spectrometry according to embodiments of the inventive concept, the MALDI imaging mass spectrometry is characterized in measuring a distribution of a treated drug in a biotissue. In an angiogenesis inhibition determining method using MALDI mass spectrometry according to embodiments of the inventive concept, the MALDI image mass spectrometry is characterized in measuring resolution in a range equal to or lowers than 30 μm.

In the angiogenesis inhibition determining method using MALDI mass spectrometry according to embodiments of the inventive concept, if concentration of treating the voacangine is X mM and intensity of the voacangine peak expressed in a range from 360 to 380 m/z is Y, Y/X may be 1450 to 1550. In other words, in the angiogenesis inhibition determining method using MALDI mass spectrometry according to embodiments of the inventive concept, voacangine concentration X and voacangine peal intensity of a range from 360 to 380 after MALDI mass spectrometry may be proportional to each other in first dimension.

In the angiogenesis inhibition determining method using MALDI mass spectrometry according to embodiments of the inventive concept, the target protein may be VEGFR2. In an angiogenesis inhibition determining method using MALDI mass spectrometry according to embodiments of the inventive concept, a target protein may be preferred to be VEGFR2, which is known as being bound with voacangine, in the case of using the voacangine as a drug, but embodiments of the inventive concept may not be restrictive hereto. Additionally, a target protein binding bound with a drug which is being used may be preferred to be selected in accordance with the drug, and embodiments of the inventive concept may not restrict the target protein, which is bound therewith, to VEGFR2 even in the case that a selected drug is voacangine.

In an angiogenesis inhibition determining method using MALDI mass spectrometry according to embodiments of the inventive concept, the target protein may be preferred to be detected through immunofluorescence, but embodiments of the inventive concept may not be restrictive hereto and may use various methods for detecting target proteins which are known those skilled in the art.

In the angiogenesis inhibition determining method using MALDI mass spectrometry according to embodiments of the inventive concept, the MALDI mass spectrometry may be MALDI Time-Of-Flight (MALDI-TOF) mass spectrometry or MALDI quadrupole ion trap (MALDI QIT).

In an angiogenesis inhibition determining method using MALDI mass spectrometry according to embodiments of the inventive concept, a mass value measured by a MALDI mass spectrometer may mean one taken in a positive mode of a MALDI-TOF mass spectrometer.

Throughout the specification, many articles and patent documents are cited and introduced as references. These disclosures of articles and patent documents will be interstitially referred to explain the level of the technical art relevant to the inventive concept and to clarify the embodiments of the inventive concept.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Hereafter, embodiments of the inventive concept will be described below in conjunction with the accompanying figures, but the inventive concept may not be restrictive to the following embodiments.

<Experimental Materials>

Voacangine and 12-methoxyibogamine-18-carboxylix acid were purchased from THC Plarm (Frankfurt, Germany). Sunitinib malate (SU11248) was purchased from Imagene (Seoul, Korea). Trifluoro-acetic acid (TFA), methanol (MeOH), and α-cyano-4-hydroxy cinnamic acid (CHCA), which is a matrix compound, were purchased from Sigma-Aldrich (St. Louis, Mo.). Acetonitrile (ACN) was purchased from Merck (Darmstadt, Germany).

<Embodiment 1> MALDI Mass Spectrometry for Voacangine

α-cyano-4-hydroxycinnamic acid (α-CHCA, Sigma Aldrich, St. Louis, Mo.) of 7.5 mg/mL was dissolved in acetonitrile (ACN) of 50% to manufacture a matrix solution. Voacangine was mixed with the α-CHCA mixed matrix solution (7.5 mg/mL) and then MALDI MS spectrometry (A MALDI LTQ Orbitrap XL mass spectrometer (Thermo Fisher Scientific, Bremen, Germany) was performed.

Figure 1:
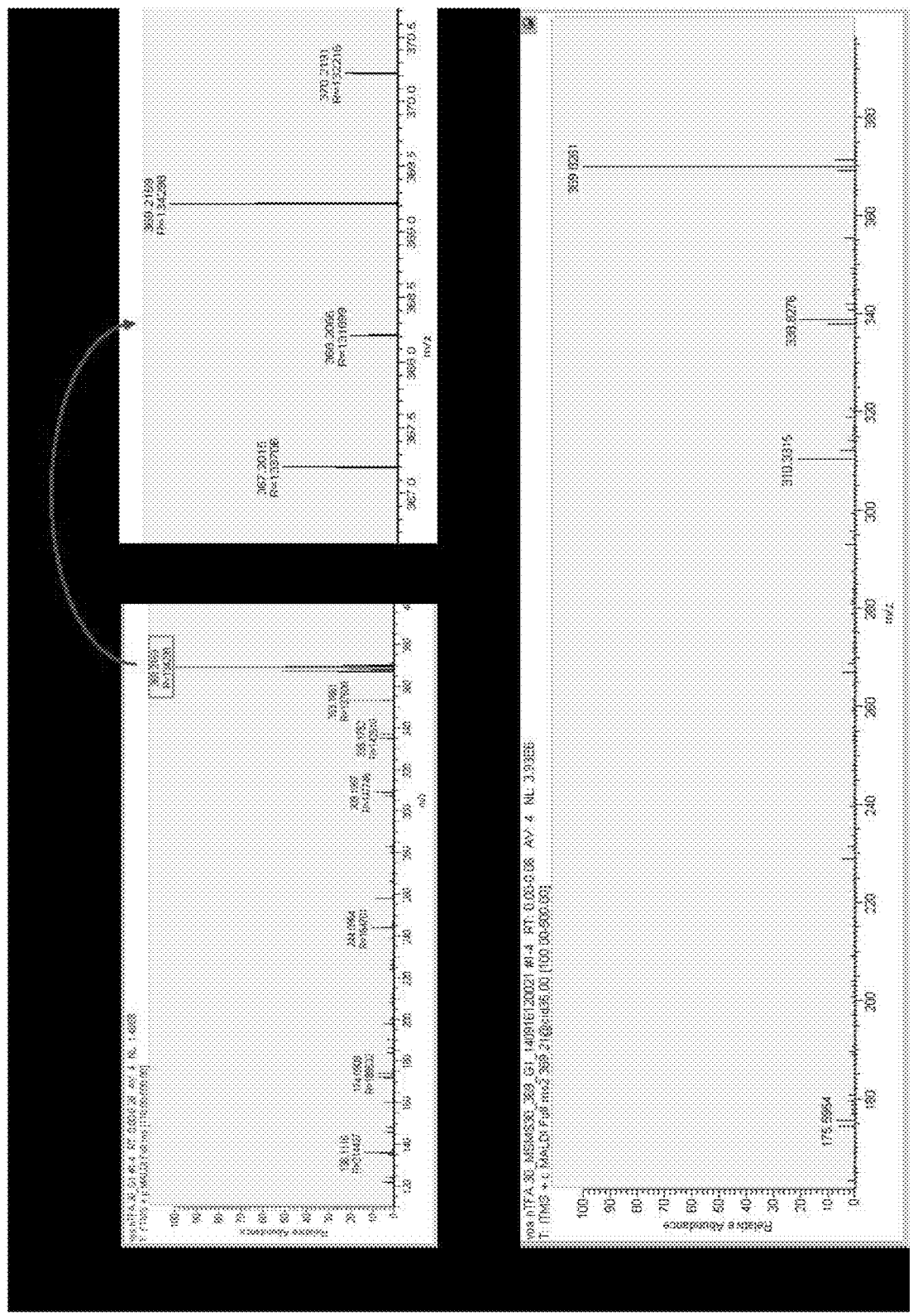
FIG. 1 shows a result of MALDI mass spectrometry with voacangine.

It can be seen from a MALDI MS plate of FIG. 1 that voacangine is intensified with the highest main peak at m/z=369.21 and has peaks at m/z 310.33 and m/z 338.82. These peaks of m/z 310.33 and m/z 338.82 are regarded as being expressed through metabolism of voacangine which is injected.

<Embodiment 2> Detecting Voacangine in Cancer Cell

<Embodiment 2-1> Settling Cancer-Diseased Animal Model and Preparing Tissue Section A cell strain U87MG, which is a kind of human glioglastoma multiforme purchased from American Type Culture Collection (ATCC), was cultivated in a medium to which Phosphate-Buffered Saline (PBS): Matrigel (1:1) is added. The cultivated cell strain U87MG of $5 \times 10^6$ was merged with PBS:Matrigel (1:1) of 100 μl and the mixture was injected into athymic nude mice for two weeks to induce growth of a cancer cell.

The induced portion of the cancer cell was separated from the mice and then a frozen section was obtained in 10 μm by using a cryostat microtome.

<Embodiment 2-2> Quantitative Analysis Using Tissue Section

After treating voacangine for a cancer cell, for the purpose of analyzing a correlation between concentration of the voacangine and a result of MALDI mass spectrometry with the voacangine detected from the cancer cell, the concentration of the voacangine treated in the cancer cell section obtained from Embodiment 2-1 was differently treated to analyze the correlation between peak intensity of the MALDI mass spectrometry and each treated concentration of the voacangine.

Using a mixed solution with acetonitrile of 50% and trifluoro-acetic acid of 0.2%, the voacangine was diluted with the mixed solution in concentration of 10 nM to 1 mM in sequence. The voacangine solutions with concentration of 10 nM to mM were treated on the surface of the cancer cell section obtained from Embodiment 2-1 to manufacture cell samples, and then MALDI mass spectrometry was performed respectively for the cell samples. This result was shown in FIG. 2.

Figure 2:
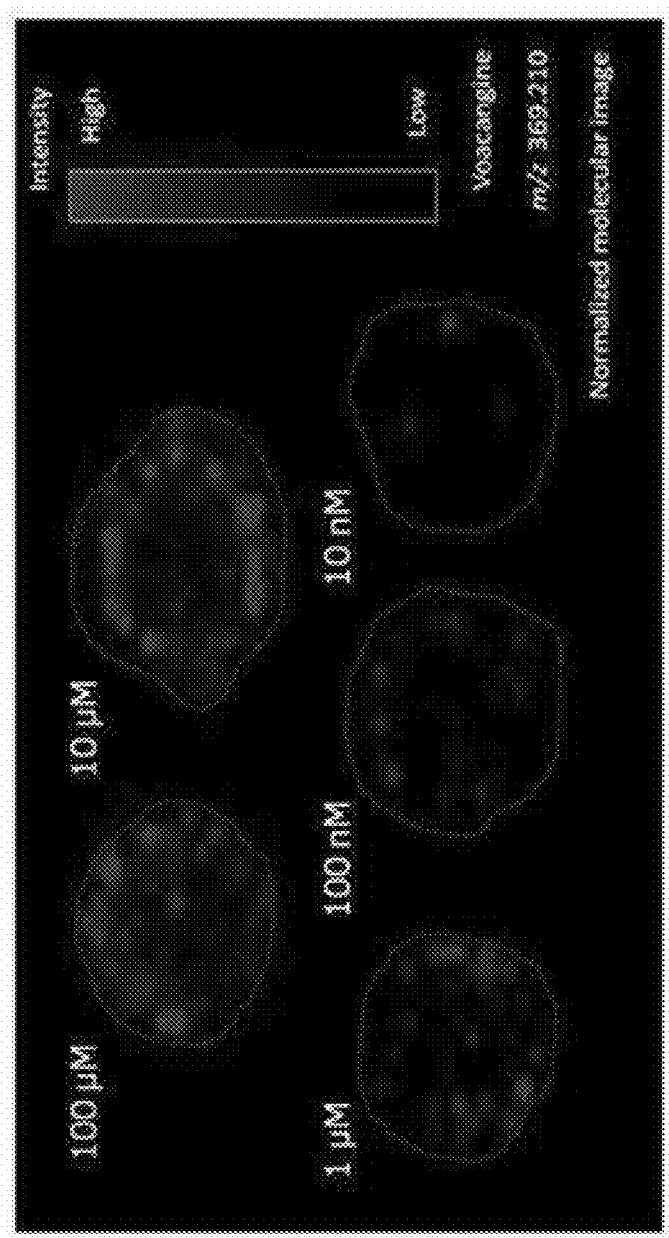
FIGS. 2 and 3 show a result of MALDI mass spectrometry according to concentration of voacangine in a cell.
Figure 3:
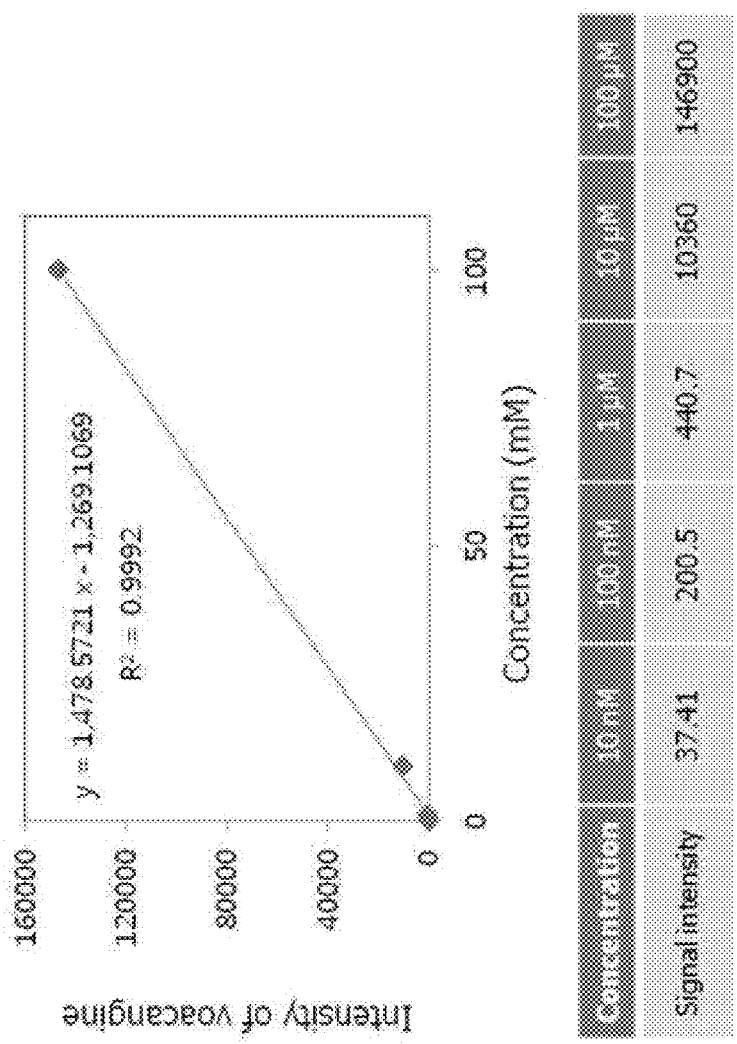

FIG. 3 shows a correlation between results of detection intensities of MALDI mass spectrometry in cancer cell sections according to voacangine concentration measured as embodied in FIG. 2. As shown in FIG. 3, provided that concentration of voacangine in a cell between cancer cell voacangine concentration is X mM and voacangine peak intensity of MALDI mass spectrometry is Y, it can be seen that the X and Y forms a first-dimensional proportion of X/Y=1478.

It can be seen from this experimental result that it may be allowable to estimate concentration of voacangine in a cancer cell by MALDI mass spectrometry.

<Embodiment 3> Measuring Variation of Cancer Size According to Dosage of Voacangine After settling a cancer-diseased animal model by injecting a cell strain U87MG into mice as shown in Embodiment 2-1, the mice induced to a cancer after two weeks were classified into three groups as given in Table 1. Voacangine (10 mg/Kg), sunitinib (40 mg/Kg) as a comparative example, and vehicle (saline:EtOH:Tween 80 (97.8:2:0.2) as another comparative example were dosed respectively into the three groups every day for 12 days in the condition of Table 1.

TABLE 1

| | Vehicle | Voacangine | Sunitinib |
|---|---|---|---|
| Number of mouse | 6 | 6 | 5 |
| Drug treatment | Vehicle 100 μl | 10 mg/kg | |
| | (i.p) | | |
| | 100 μl | 40 mg/kg | |
| | (p.o) | | |
| | 100 μl | | |

Figure 4:
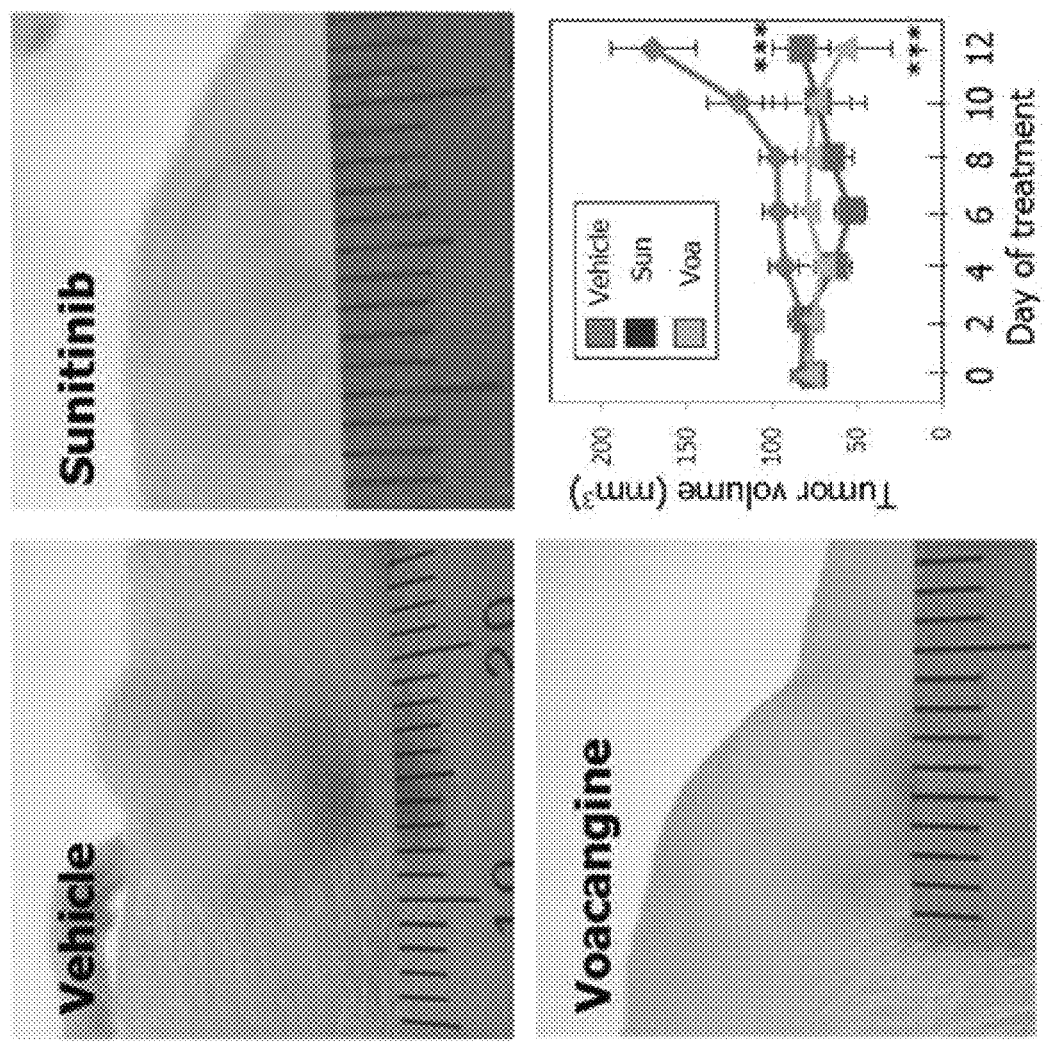
FIG. 4 show a result taken from a variation of a cancer size by dosing voacangine into a cancer-diseased animal model.

From FIG. 4, it can be seen that a cancer size after dosage of voacangine is greatly reduced than the case of dosing vehicle as a comparative example and the case of dosing sunitinib as another comparative example.

<Embodiment 4> Measuring Voacangine Distribution

Figure 5:
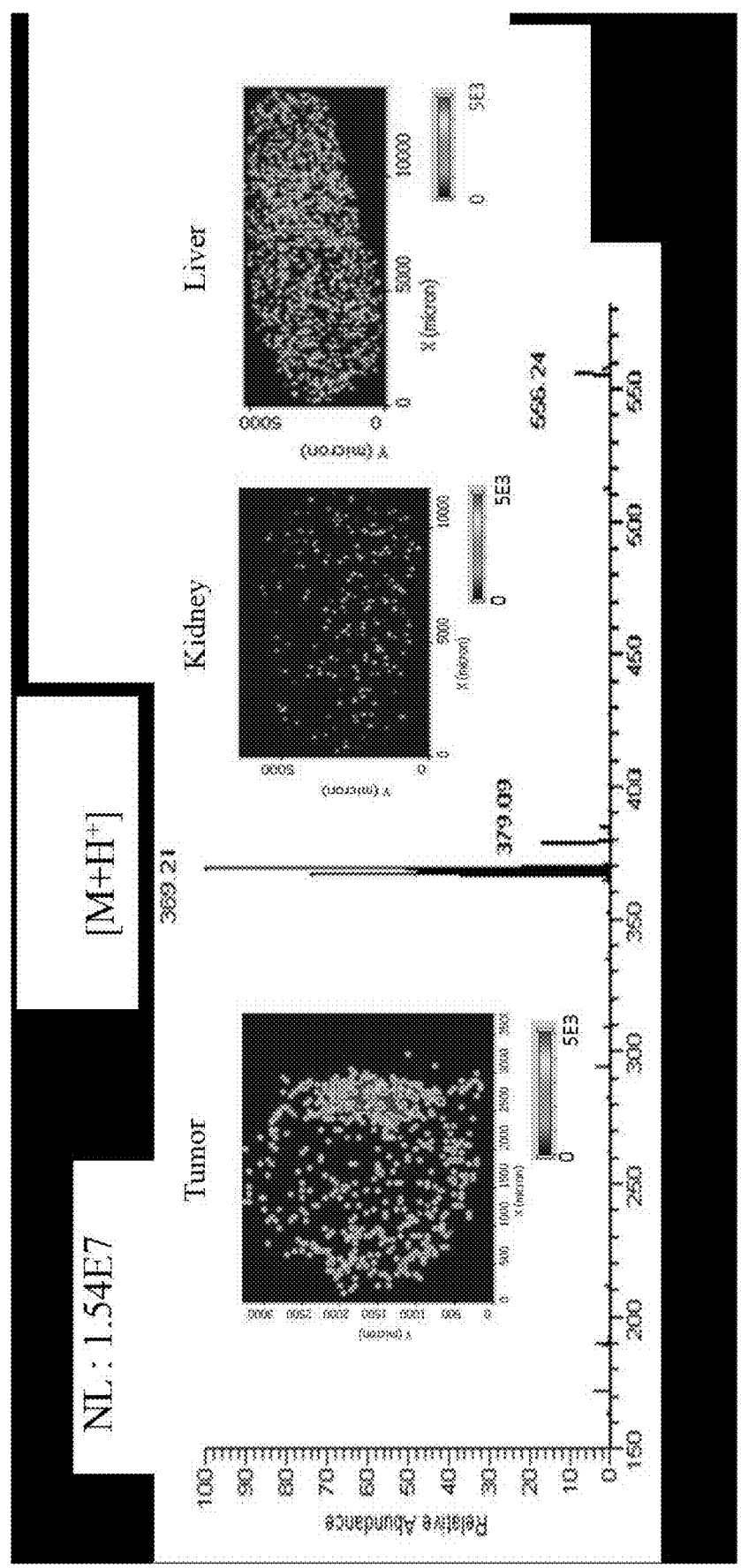
FIG. 5 show a result of measuring a distribution of voacangine in a cancer-diseased animal model by using MALDI imaging mass spectrometry after dosing the voacangine into the model.
Figure 6:
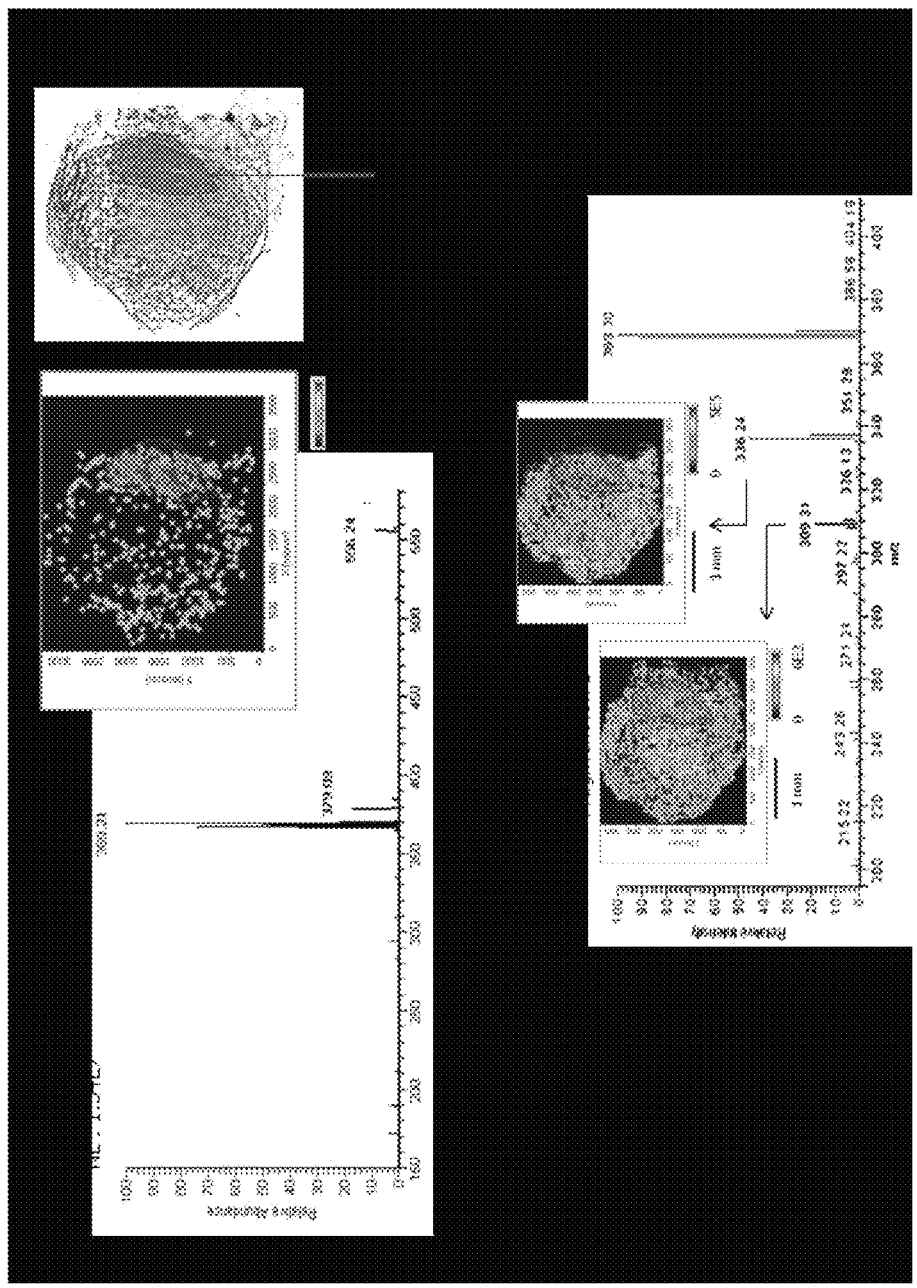
FIGS. 6 and 7 show results of comparing MALDI imaging mass spectrometry with general immunofluorescence in the case of injecting voacangine, sunitinib, and vehicle.

After surgically removing tumors, livers, and kidneys from mouse models after four hours after treating voacangine in Embodiment 3, a specimen was manufactured to perform MALDI mass spectrometry and immunofluorescence with H&E straining and the result was shown in FIG. 5.

From FIG. 5, it can be seen that in the case of treating voacangine, the voacangine is localized in livers, kidneys, and cancer cells, being more concentrated in the cancer cells than the livers and kidneys.

<Embodiment 5> Measuring Drug Distribution in Separated Cancer Cell

After treating voacangine, sunitinib, and vehicle in a cancer-diseased animal model induced as described in Embodiment 2-1, a portion of cancer cell was independently separated and treated by H&E straining through immunofluorescence. Then, the result was compared with a result of MALDI mass spectrometry.

Figure 7:
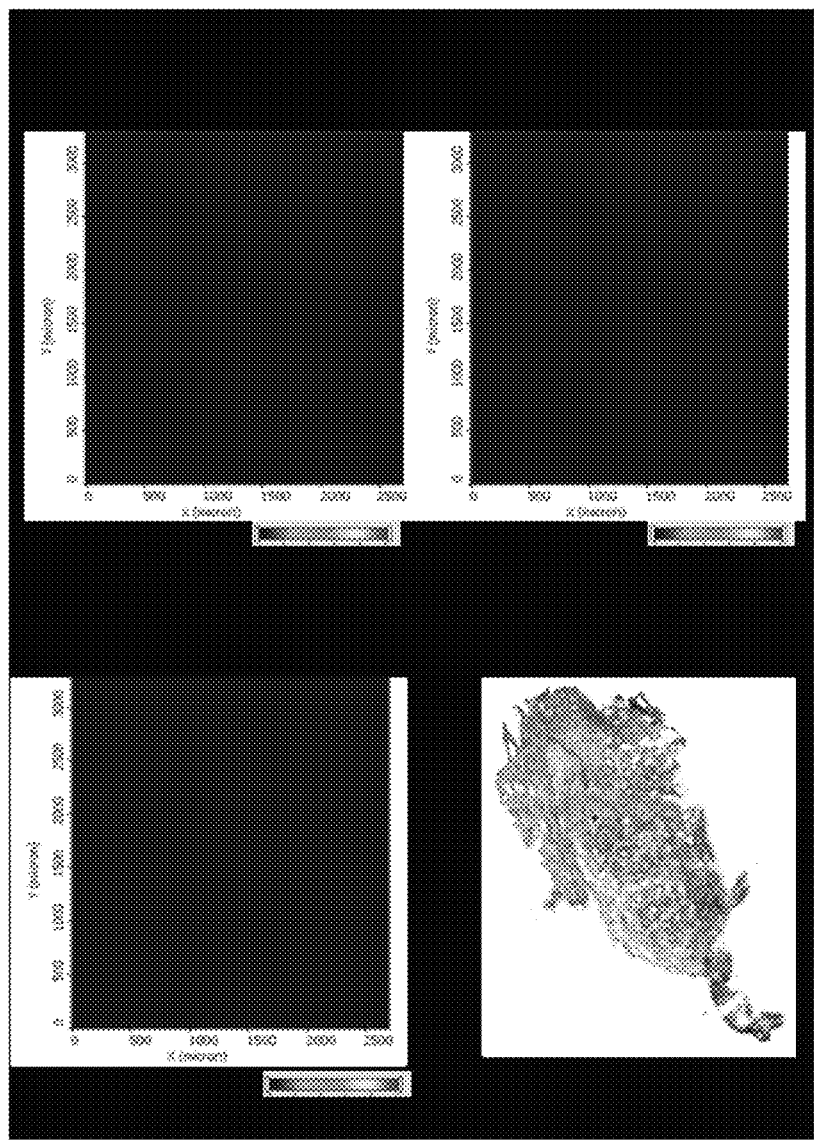

It can be seen that, while the case of voacangine is identical to a result of MALDI imaging mass spectrometry according to an embodiment of the inventive concept and a result of the H&E straining spectrometry, the case of injecting vehicle is failed to detect the vehicle even by the MALDI imaging mass spectrometry as shown in FIG. 7. Accordingly, it can be found that the MALDI imaging mass spectrometry peculiarly affects voacangine in a cancer cell.

<Embodiment 6> Measuring Binding State with Target Protein

For the purpose of detecting whether voacangine was bound with a target protein and measuring a distribution of binding between the voacangine and the target protein, the cancer cell sections manufactured as described in Embodiment 2-1 were marked respectively by anti-EGFR1 (1:50 Abcam, Cambridge, Mass.), anti-FGFR1 (1:50 Cell Signaling Technology, Danvers, Mass.), anti-FGFR (1:50, Santa Cruz), and anti-VEGFR2 (1:50, Cell Signaling Technology, Danvers, Mass.) and thereafter dyed by DAPI (Invitrogen, Eugene, Oreg.).

Figure 8:
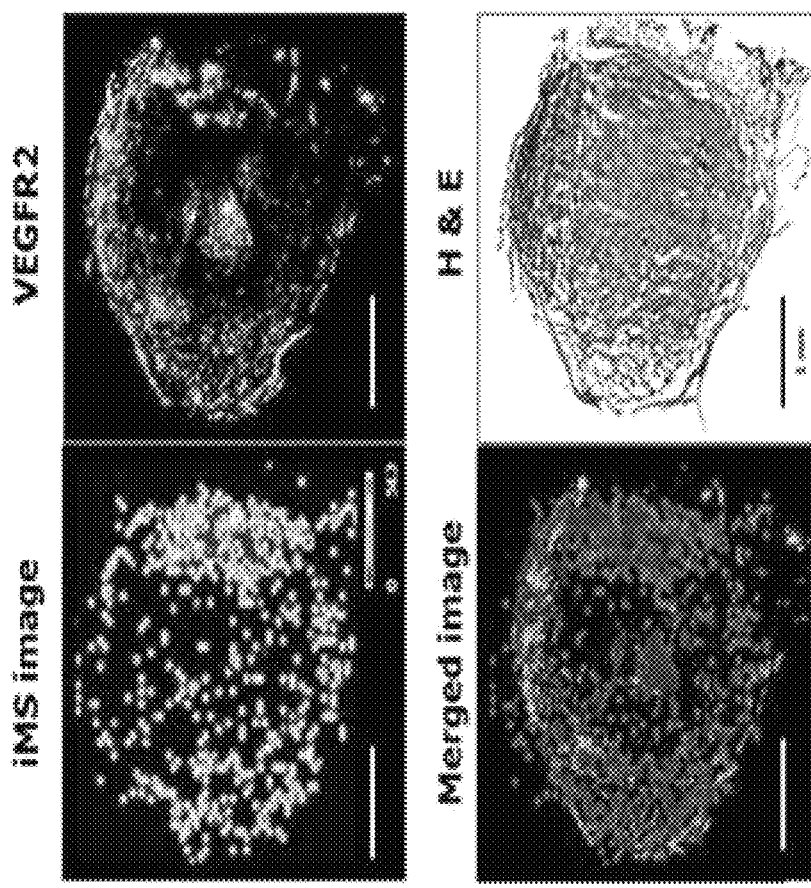
FIG. 8 shows a result of comparing a result of comparing a result of MALDI imaging mass spectrometry according to an embodiment of the inventive concept with a result of dyeing a target protein by general immunofluorescence.
Figure 9:
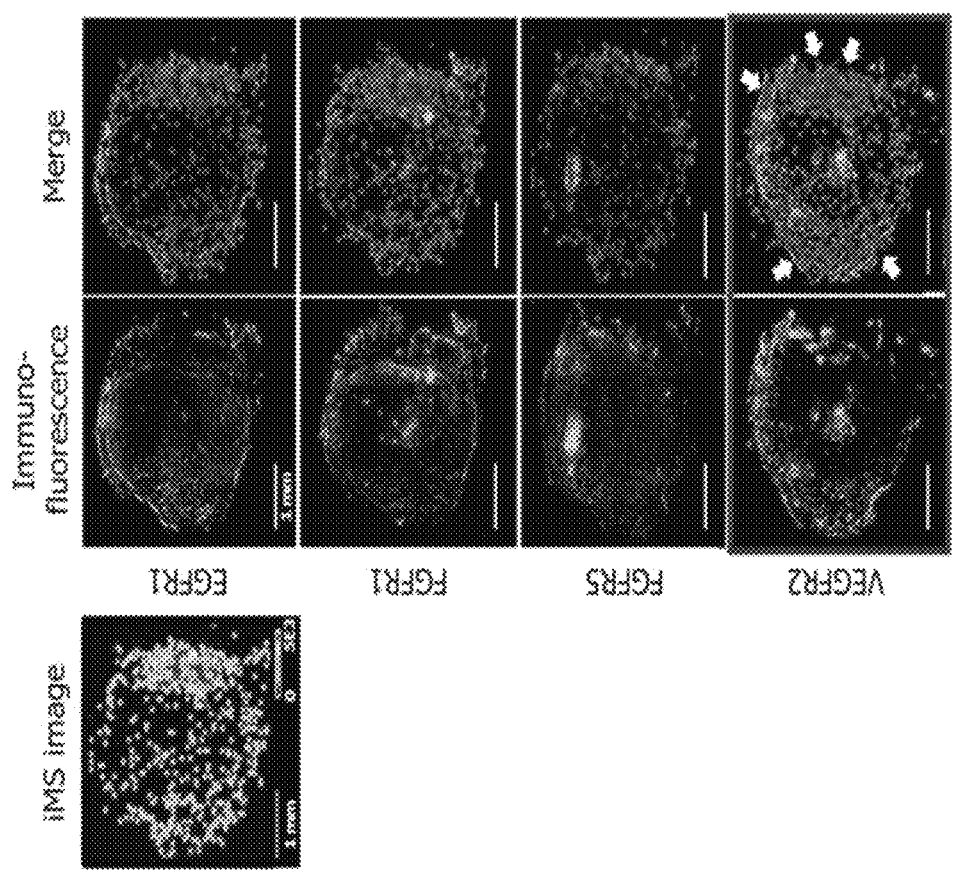
FIG. 9 shows binding states and distributions between voacangine and target proteins in a cancer cell.

The dyed cells were taken into photographs by using confocal Laser Scanning Microscope (LSM 700, Carl Zeiss, Thornwood, N.Y.), resulting in FIGS. 8 and 9.

FIG. 8 was obtained from comparison between a result of MALDI mass spectrometry according to an embodiment of the inventive concept and general immunofluorescence. It can be seen from FIG. 9 that a merged image with results of MALDI mass spectrometry and immunofluorescence shows a binding state between voacangine and target proteins and their distribution in a cancer cell.

Figure 10:
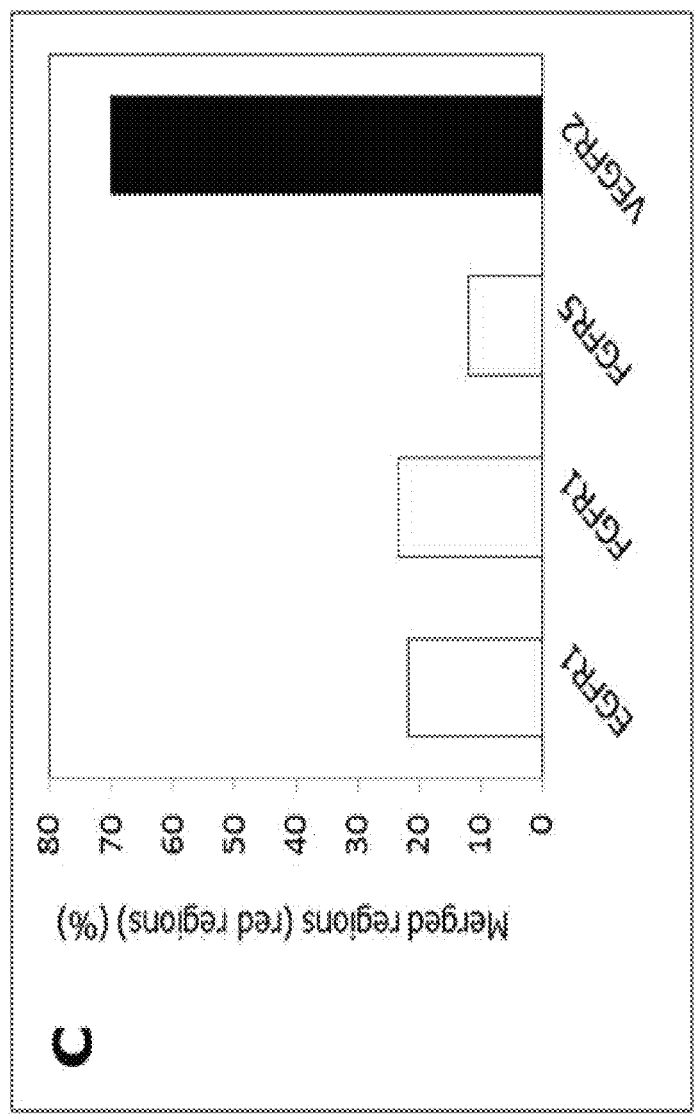
FIG. 10 shows a result digitizing expression levels of target proteins in a merged image with a result of MALDI imaging mass spectrometry and a result of immunofluorescence.

A result digitizing expression levels of target proteins in a merged image with results of MALDI mass spectrometry and immunofluorescence was shown in FIG. 10.

It can be seen from FIG. 10 that voacangine is peculiarly bond with VEGFR2.

<Embodiment 7> Measuring a Binding Rate Between Voacangine and Target Protein by Western Blot Western blot is used for detecting whether voacangine was bound with a target protein VEGFR2.

Figure 11:
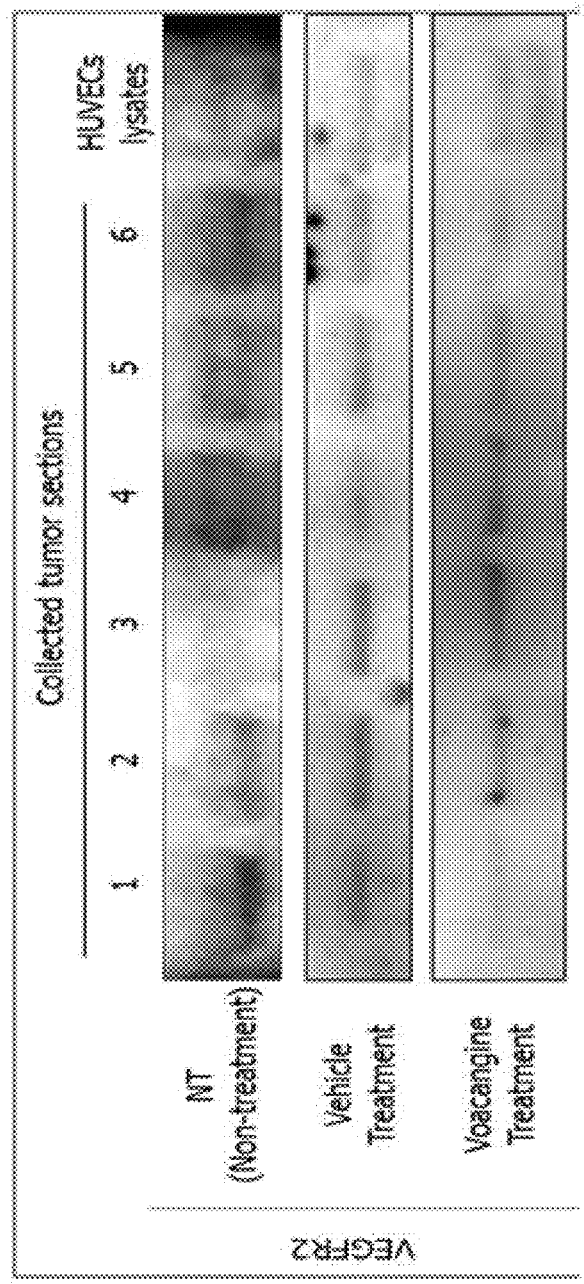
FIG. 11 shows a result of detecting whether voacangine is bound with a target protein VEGFR2 by Western blot.

In detail, a Radioimmuno Precipitation Assay (RIPA) buffer (Cell Signaling Technology, USA) was used to crush a cell, then obtaining a cell extract. After expanding the cell extract of 10 μg over Sodium Dodecyl Sulfate-Polyacrylamide gel Electrophoresis (SDS-PAGE) and separating a target protein therefrom, a first antibody and a second antibody were used to ascertain expression of VEGFR2 in sequence, resulting in FIG. 11.

TABLE 2

| Target protein | Primary Antibody | Secondary Antibody |
|---|---|---|
| VEGFR2 (200 kDa) | 1:250 | 1:10000 (mouse) |

<Embodiment 8> Detecting Voacangine in Cancer Cell

Figure 12:
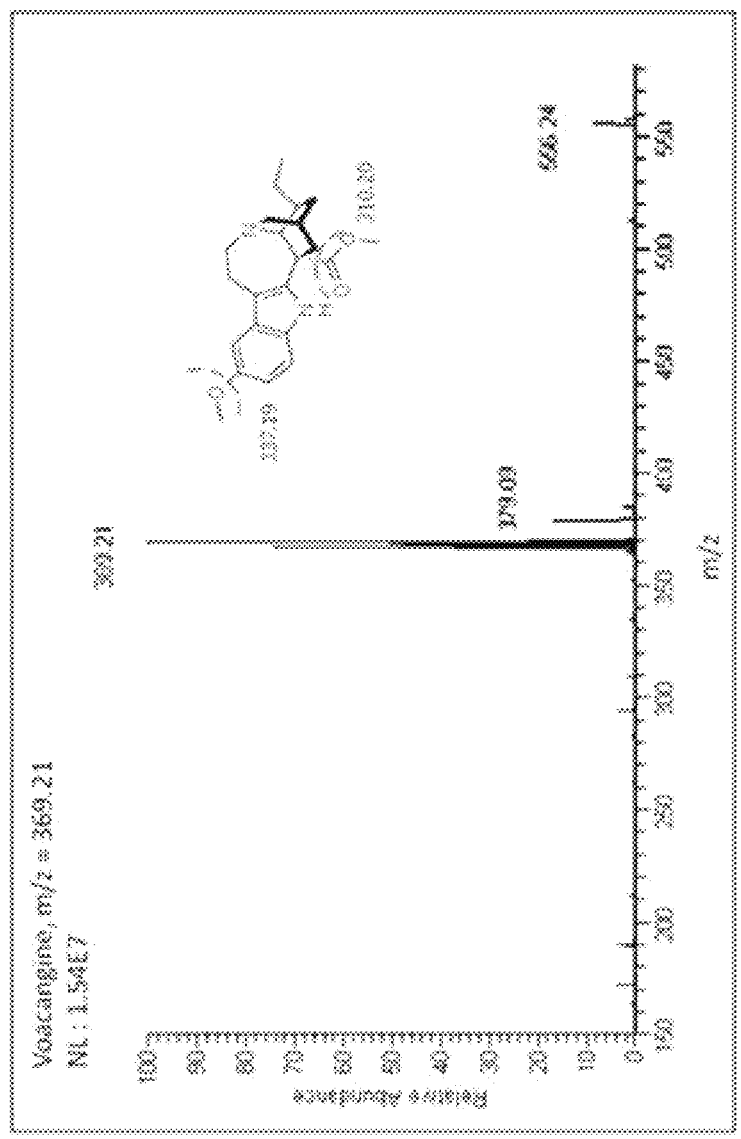
FIGS. 12 and 13 show results of performing MALDI mass spectrometry with a cancer cell.
Figure 13:
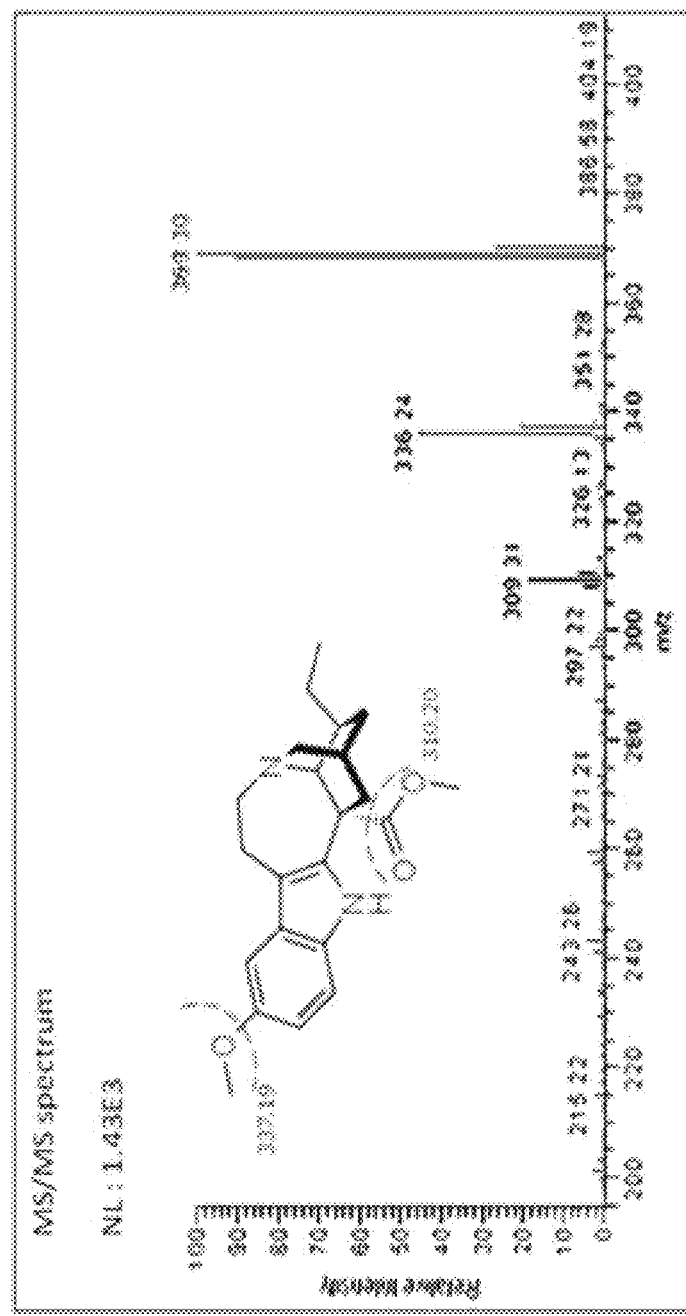

A result of performing MALDI mass spectrometry in a cancer cell tissue obtained from Embodiment 7 was shown in FIGS. 12 and 13.

It can be seen from FIGS. 12 and 13 that voacangine is detected in the cancer cell tissue, and peaks expressed at 336.24 m/z and 309.31 m/z are due to fragments and caused from metabolism in the tissue after treatment of the voacangine, inducing a chemical change of the voacangine.

<Embodiment> Measuring Expression Level of CD31 by Voacangine

Immunohistochemical analysis was performed to find an effect of voacangine against pathological angiogenesis of a cancer cell.

CD31 or Platelet Endothelial Cell Adhesion Molecule-1 (PECAM-1) are known as being expressed on the surface of a hematoblast such as platelet and naive T cell, natural killer cell, granulocyte, monocyte and cell-to-cell junction of endothelial as transmembrane glycoprotein of 130 kDa type belonging to immunoglobulin super-family.

Figure 14:
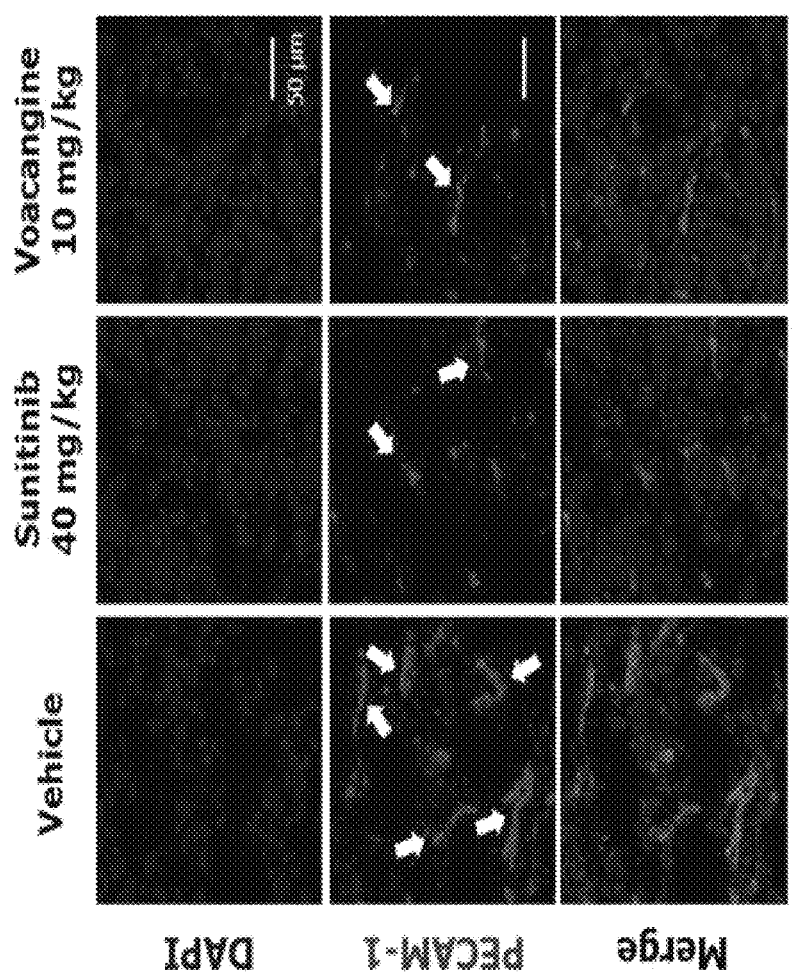
FIGS. 14 and 15 show results of measuring expression level of CD31 by dosing voacangine and sunitinib.
Figure 15:
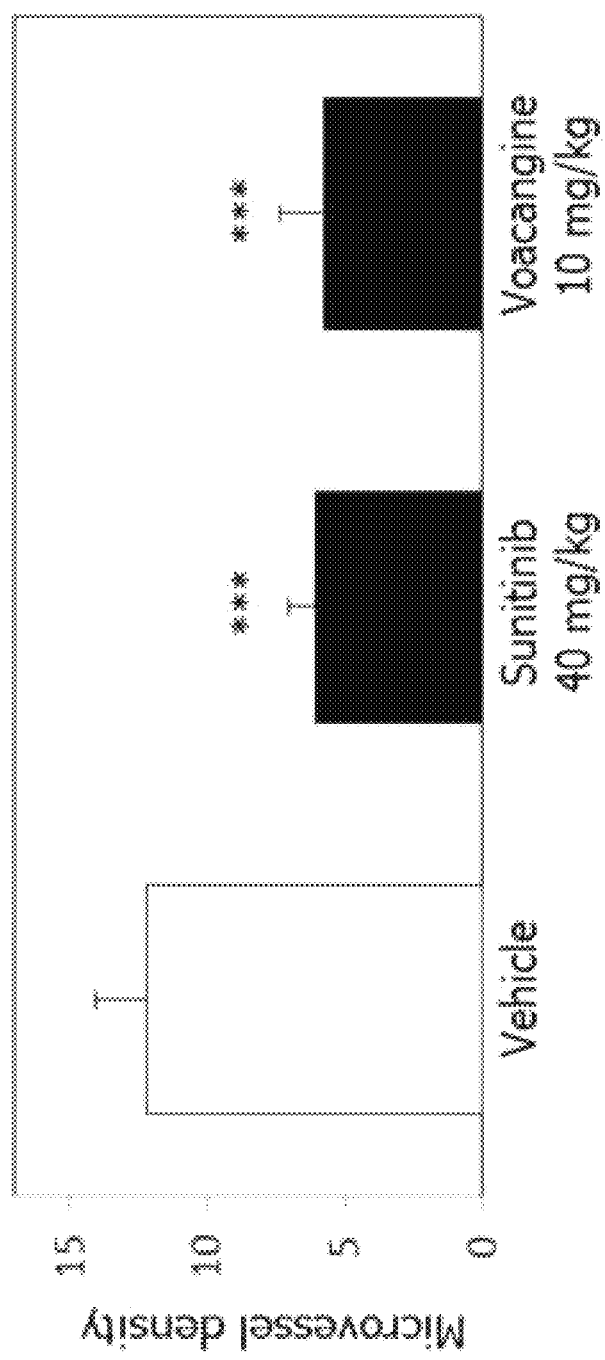

It can be seen from FIGS. 14 and 15 that CD31 is greatly reduced in expression when dosing voacangine and sunitinib.

As described above, an angiogenesis inhibition determining method using MALDI mass spectrometry according to embodiments of the inventive concept may detect a distribution state of small molecules in addition to voacangine, without an indicator, by using MALDI mass spectrometry, finding whether the small molecules as well as voacangine are bound with a target protein and measuring distributions of the bound small particles and target protein in comparison with a result of immunofluorescence for the target protein, and then may determine to inhibit angiogenesis from the measured result.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:
1. A method for determining distribution of a small molecule drug relative to a target protein in angiogenesis inhibition using MALDI mass spectrometry and immunofluorescence, the method comprising:
   obtaining a sample;
   treating the sample with a small molecule drug;
   performing MALDI mass spectrometry on the sample treated with the small molecule drug;
   detecting a target protein for the small molecule drug in the sample by immunofluorescence;
   comparing a result of the MALDI mass spectrometry with a result of immunofluorescence for the target protein; and determining whether angiogenesis is inhibited in a portion of the sample overlapping with both (i) a portion where the small molecules are present after the MALDI mass spectrometry and (ii) a portion where the target protein is present after immunofluorescence, wherein the small molecule drug is voacangine given in Formula 1 as follows, <Formula 1>

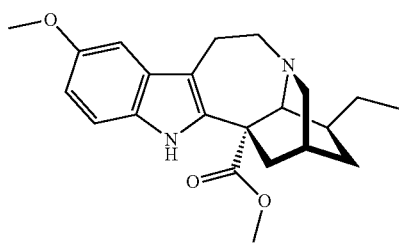

and wherein the target protein is VEGFR2, wherein the MALDI mass spectrometry for the voacangine-treated sample shows peaks in the ranges 360 to 380 m/z, 330 to 340 m/z, and 300 to 310 m/z, so as to thereby determine distribution and concentration of the small molecule drug relative to target protein in angiogenesis inhibition.

2. The method of claim 1, wherein the MALDI mass spectrometry for the voacangine-treated sample shows a main peak at 369.21 m/z and shows peaks at 336.24 m/z and 309.31 m/z.

3. The method of claim 1, wherein the MALDI mass spectrometry is MALDI imaging mass spectrometry.

4. The method of claim 1, wherein the MALDI mass spectrometry is MALDI quadrupole ion trap (MALDI QIT).

* * * * *